United States Patent [19]
Moake et al.

[11] Patent Number: 4,880,788
[45] Date of Patent: Nov. 14, 1989

[54] METHOD FOR PREVENTING AND TREATING THROMBOSIS

[75] Inventors: Joel L. Moake; Martin D. Phillips; Larry V. McIntire; Jesse D. Hellums, all of Houston, Tex.

[73] Assignee: Baylor College of Medicine, Houston, Tex.

[21] Appl. No.: 115,236

[22] Filed: Oct. 30, 1987

[51] Int. Cl.$^4$ .................. C07C 105/00; C07C 107/00
[52] U.S. Cl. .................................... 514/150; 514/570; 514/824; 514/822
[58] Field of Search ................. 51/814, 815, 822, 824, 51/150, 570

[56] References Cited

U.S. PATENT DOCUMENTS

| | | | |
|---|---|---|---|
| 3,985,884 | 10/1976 | Conrow et al. | 424/269 |
| 3,998,957 | 12/1976 | Conrow et al. | 424/273 |
| 4,007,270 | 2/1977 | Bernstein et al. | 424/230 |
| 4,027,038 | 5/1977 | Bernstein et al. | 424/315 |
| 4,087,548 | 5/1978 | Lenhard et al. | 424/315 |
| 4,103,028 | 7/1978 | Bernstein et al. | 424/315 |
| 4,182,774 | 1/1980 | Welstead et al. | 514/539 |
| 4,313,949 | 2/1982 | Shanklin et al. | 514/237.5 |
| 4,382,955 | 5/1983 | Takita et al. | 424/309 |
| 4,619,928 | 10/1986 | Takahashi et al. | 514/356 |
| 4,659,732 | 4/1987 | Stegelmeier et al. | 548/365 |
| 4,721,713 | 1/1988 | Hayashi et al. | 514/255 |

OTHER PUBLICATIONS

Corb; et al. J. Biol. Chem., vol. 263(25), The Human Leukocyte Adhesion Glycoprotein Mac-1 (Complement Receptor Type 3, CDIIB) & Subunit (1988), pp. 12403–12411.
Aihara et al., Blood 63:495–501 (1984).
Bockenstedt et al., J. Clin. Invest. 77:743–749 (1986).
Ceramo et al., Scientific American 256:90–96 (1987).
Cooper et al., J. Lab. Lin. Med. 90:512–521, (1977).
Fitzsimmons et al., Thrombos. Haemost. 56:95–99 (1986).
Geratz et al., Thrombos. Haemost. 39:411–425 (1978).
Giger et al., Agents and Actions 4(3):173–179 (1974).
Houdijk et al., J. Clin. Invest. 75:531–540 (1985).
Kirby, Thrombos, Diathes, haemorrh, 34:770–779 (1975).
Leytin et al., Thrombosis Research 34:51–63 (1984).
Moake et al., Clinical Symposia 37(4):1–32 (1985).
Moake et al., J. Clin. Invest. 78:1456–1461 (1986).
Moake et al., New England Journal of Medicine 307:1432–1435 (1982).
Peterson et al., Blood 69:625–628 (1987).
Moake et al., Blood 68 (Suppl 1):332a (1986).
Moake et al., Blood 64:592–598 (1984).
Wick et al., J. Clin. Invest. 80:905–910 (1987).

Primary Examiner—H. M. S. Sneed
Assistant Examiner—J. Saba
Attorney, Agent, or Firm—Fulbright & Jaworski

[57] ABSTRACT

The present invention provides a method for preventing and treating thrombosis in an individual comprising administering a compound effective to inhibit the agglutination and aggregation of blood platelets to an individual in need of said treatment. In a preferred embodiment, the compound is selected from the group consisting of aurin tricarboxylic acid, triphenyl methyl dyes, substituted naphthalene sulfonic acid moieties, the analogs and agonists of these compounds and pharmaceutically acceptable salts thereof.

13 Claims, 11 Drawing Sheets

METHOD FOR PREVENTING AND TREATING THROMBOSIS

BACKGROUND OF THE INVENTION

1. Field of the Invention

The present invention relates to a method of preventing and treating thrombosis, acute crisis in sickle cell anemia, neoplastic metastases and certain aging disorders.

2. Description of the Background Art

Arterial and venous thromboemboli cause common, serious or life-threatening disorders. Coronary arterial thrombosis leads to coronary ischemia and infarction. Thrombotic or embolic occulusions of cerebral arteries may result in ischemia or infarction of the central nervous system. Venous thrombic disorders are associated with emboli that occlude branches of the pulmonary arterial circulation and frequently complicate the course of other serious illnesses or the recovery from injury or surgery.

Therapeutic recommendations for thromboembolic disorders remain controversial and are sometimes confusing. Recent studies have provided considerable insight into the pathophysiology of these disorders. In order to understand the thromboembolic phenomena, an understanding of normal hemostasis is necessary. To summarize briefly, vascular injury initiates a sequence of events that results in the formation of a platelet-fibrin barrier to limit escape of blood. The initial vessel damage exposes sub-endothelial structures to the bloodstream, and blood platelets begin to adhere and aggregate at the site of injury due to their interaction with factor VIII-related von Willerbrand factor (vWF) and collagen. Proteins of the coagulation system are also activated to generate the enzyme thrombin. Thrombin cleaves plasma fibrinogen into fibrin monomers, which polymerize around the clumped platelets and hold them in place, forming the primary hemostatic plug. Over the following 8-24 hours, additional fibrin is laid down, forming the secondary hemostatic plug and allowing the repair of the underlying vessel wall to proceed. Subsequently, this clot is digested by the fibrinolytic enzyme, plasmin, which is activated in situ (Moake, *Clinical Symposia,* Volume 35, No. 3, 1, 1983).

One of the major physiologic mechanisms of platelet thrombus formation is vWF-mediated platelet aggregation. Much is known about the interaction of vWF with its major receptor, glycoprotein Ib (Bockenstedt, et al., *J. Clin. Invest.* 77: 743, 1986), but there are no specific chemical inhibitors of this binding in common use. Additionally, there are situations in which a drug to interrupt this association in humans may be beneficial. These includes coronary and cerebral thrombosis, thrombotic thrombocytopenic purpura and the hemolytic-uremic syndrome.

vWF is a large, multimeric plasma protein (subunit molecular weight of $2.25 \times 10^5$ daltons) synthesized by bone marrow megakaryocytes and endothelial cells that form the lining of blood vessels. Circulating vWF is heterogeneous in size, with multimers ranging from about $4 \times 10^5$ to millions of daltons. Large vWF multimeric forms are involved in platelet-subendotheial adhesion and in shear stress-induced platelet aggregation. Large vWF forms bind to platelet surfaces via glycoprotein molecules embedded in the cell membrane.

Human endothelial cells in culture synthesize "unusually large" vWF multimers which are larger than the largest multimeric forms found in normal human plasma ("plasma-type" vWF multimers). These unusually large vWF forms are secreted by endothelial cells into the subendothelial matrix and, under certain conditions, into the plasma. The unusually large vWF multimers are very adhesive to platelets. When endothelial cells are damaged, platelets adhere to collagen and vWF multimers, perhaps especially the unusually large forms in the exposed subendothelium.

In the arterial circulation, the platelet adhesion and aggregation that follows vascular damage may sometimes lead to arterial thrombosis. If a platelet thrombus forms and completely or substantially occludes the arterial lumen, blood flow is slowed or stopped distal to the occlusion. This diminished blood flows leads to coagulation factor activation, thrombin generation, fibrin polymer formation, and additional thrombin-induced platelet aggregation distal to the site of vessel injury. As a result, the initial thrombus, composed predominantly of platelets, extends distally as fibrin formation occurs. Arterial emboli (portions of thrombi that break away into the bloodstream) may also partially or completely occlude distal arterioles or capillaries, causing ischemia or infarction of the tissues supplied by these vessels. Emboli originating from a thrombus on an atherosclerotic cerebral artery can cause transient partial occlusion of a distal vessel (transient ischemic attack) or complete vascular occlusion and infarction of brain tissue (stroke).

Thrombotic thrombocytopenic purpura (TTP) and the hemolytic-uremic syndrome (HUS) are diseases caused by platelet aggregation in the arterial circulation. In TTP, the formation of platelet clumps occurs in the arterial system, resulting in the occlusion of some arterioles and capillaries. In HUS, the intravascular platelet clumping is confined almost exclusively to the renal arterial vessels. In both syndromes, the intravascular clumping of platelets is the cause of the thrombocytopenia. In addition, erythrocyte fragmentation occurs in both disorders because red blood cells are injured as they move through the partially occluded arterioles and capillaries.

In 1975, Kirby reported that Evans Blue, a common dye formerly used in biological laboratories for blood volume determination, interrupted the association of formaldehyde-fixed human platelets with human vWF and ristocetin, or bovine vWF alone. (Kirby, *Thhrombos Diathes Haemorrh.* 34: 770, 1975.) This reaction is properly termed platelet agglutination, which is the clumping of platelets induced by vWF binding to the platelet surface, mostly via glycoprotein Ib, and is not necessarily associated with a secondary platelet granule release reaction. In contrast, platelet aggregation requires functional, metabolically-active platelets. Platelet aggregation is induced by a variety of stimuli, including ADP, collagen or arachidonic acid and results in irreversible platelet shape change and granule release. Subsequently, Geratz et al. (*Thrombos Haemostas* 39: 411, 1978) tested 20 custom synthetic compounds with structural similarity to Evans Blue and found that minor changes in substituent groups on the phenol rings altered the platelet aggregation-inhibitory activity of these compounds and, in some cases, caused a differential change in the anti-aggregation and anti-agglutination activities. In their assay system, suramin (an antitrypanosomal drug) was a weak anti-aggregation agent.

In vitro, ristocetin (a negatively-charged antibiotic) or fluid shear stresses alter the platelet surface so that vWF multimers attach to the platelets and cause them to clump.

Unusually large vWF multimers, which resemble those synthesized by normal human endothelial cells in culture, have been found in the plasma of some patients with the chronic relapsing type of TTP. These unusually large vWF multimers are not found in normal plasma. The plasma content of unusually large vWF multimers decreases during relapses in this disorder, presumably because they have become attached to agglutinating platelets. A mechanism similar to that of ristocetin causing in vitro attachment of vWF to platelet surfaces may be present intermittently in chronic relapsing TTP. Cationic peptides or other molecules released periodically from injured tissue or phagocytic cells may induce the selective attachment of unusually large vWF multimers to circulating platelets, and thus cause the platelets to agglutinate within arterioles. In the acute, non-relapsing type of TTP, unusually large vWF multimers may enter the circulation as a result of extensive endothelial cell injury or stimulation.

Prior to the present invention the preferred therapy of TTP and HUS consists of prophylactic or therapeutic transfusion of normal plasma, which may provide both temporary additional vWF depolymerase activity and additional plasma proteins to bind and eliminate the proposed inciting agents in clinical relapses. During severe episodes, partial removal of the unusually large vWF multimers by plasmapheresis, combined with transfusion of normal plasma, is often required to control platelet agglutination.

It has been suggested that HUS may be a variant of nonrecurrent TTP with intravascular platelet clumping confined to renal vessels. Recent findings indicate that large vWF multimers may also be involved in the pathophysiology of HUS, perhaps as a result of renal endothelial cell injury (or intense stimulation). Attempts to treat TTP and HUS with drugs such as acetylsalicylic acid (ASA, or aspirin), ibuprofen-type compounds (Motrin, Advil, etc.), imidazole compounds, and dipyridamole, which either directly or indirectly suppress the release of platelet granule contents (including ADP from dense granules and PDGF from a-granules) haven been of equivocal benefit. Because blood flow slows in leg veins of patients confined to bed or in those with increased intraabdominal pressure (for example, during pregnancy) coagulation factors are more likely to be activated excessively under these hemodynamic conditions. There may also be some regional increase in vWF-mediated platelet-subendothelial interaction. The resulting venous thrombosis in an iliac or deep femoral vein may cause pain and swelling of the leg. Fragments of thrombi in pelvic, iliac, or deep femoral veins are especially likely to embolize and occlude arterial branches of the pulmonary circulation, with potentially life-threatening consequences.

Another pathological condition which involves vaso-occlusion is sickle cell anemia. Among the major manifestations of sickle cell anemia are periodic, localized, vaso-occlusive crises and chronic hemolytic anemia. Adhesion of sickle erythrocytes to the vascular endothelium has been proposed as one mechanism of vaso-occlusion. Sickle red cells adhere abnormally to cultured endothelial cell under both static and flow conditions. This increase in adhesion, when compared to normal red cells, has been related to the clinical severity of vaso-occlusive events in sickle cell disease (Hebbel, et al., *New England J. Med* 302: 992, 1980). Wick demonstrated that unusually large vWF multimers mediate the adhesive interactions between sickle erythrocytes and endothelial cells (Wick T. M., et al., *J. Clin. Invest.*, 80: 905, 1987).

Interference with platelet aggregation may inhibit the capacity of neoplastic cells to metastasize (Honn, et al. Science 212: 1270, 1981). Since von Willebrand factor has been shown to be important in the implantation of circulating tumor cell-platelet clumps under certain experimental conditions, the inhibition of vWF-mediated platelet adhesion to subendothelial surfaces by the compound useful in the present invention may decrease the chance of metastasis of certain human malignancies (Marcum, et al., *J. Cab. Clin. Med.* 96: 1046, 1980). Since vWF-platelet interactions may play a role in the aging process (Cerami, et al., *Sc. American* 256(5): 90, 1987, the compounds useful in the present invention may delay certain aging phenomena.

SUMMARY OF THE INVENTION

The present invention arose out of observations by the inventors that the agglutination of human platelets out of suspensions in vitro, when the largest human vWF multimers in normal plasma are induced to attach to them, could be inhibited by a variety of compounds with structural similarities.

The present invention arose from the observation that shear stress-induced aggregation of platelets was inhibited by polyanionic compounds with structural similarities to Evans Blue and suramin. Shear stress-induced aggregation is considered to be a model of in vivo thrombosis because human platelets are aggregated by human vWF in the shear field without the addition of exogenous agents. The only factors needed for aggregation are vWF, adenosine diphosphate (ADP), calcium ions ($Ca^{2+}$), and fresh platelets with intact surface glycoprotein receptors and metabolic function (Moake, et al., *J. Clin. Invest.* 78: 1456, 1986). Evans Blue (EB), a polysubstituted naphthalene sulfonic acid compound is effective at inhibiting platelet aggregation and vWF-mediated platelet agglutination. Aurin tricarboxylic acid (ATA), a triphenylmethyl compound, is approximately ten times more active in inhibiting platelet aggregation and agglutination per mole than Evans Blue. It probably acts by competetively inhibiting the interaction of vWF with platelet glycoprotein Ib. Triphenylmethyl dyes, substituted naphthalene sulfonic acid compounds, and other small organic molecules with high negative charge densities may be useful in ameliorating pathological conditions caused by vWF-mediated platelet (or red cell) clumping.

Another application for the present invention is the inhibition of collagen activation of platelets. The receptor for collagen on platelet surfaces is not known despite active investigation into this field. Aihara, et al., Blood 63(e): 495, 1984; Houdiji, et al., *J Clin Invest* 75: 531, 1985; Leytin, et al., *Thromb Res* 34: 51, 1984; Fitzsimmons, et al., *Thrombos Haemostas* 56: 95, 1986. Collagen causes platelets to aggregate in the absence of vWF. Therefore, another aspect of the present invention is the inhibition of collagen-induced platelet aggregation (or the disaggregation of collagen-induced platelet aggregates) and, thus, treatment or prevention of pathological conditions caused thereby. Because vWF enhances the rate of collagen-platelet aggregation, the presence of vWF bound to the platelet surface may enhance collagen-platelet binding. The present invention also comprises the treatment and prevention of pathological conditions resulting from collagen-induced platelet aggregation.

One of the inventors observed that unusually large vWF multimers occur in the arterial thrombotic disorder, chronic relapsing TTP, and that unusually large vWF multimers produced and released by human endothelial cells are functionally more effective than the largest plasma vWF forms in supporting the in vitro aggregation of platelets induced by shear stress (in the absence of ristocetin or other polycations) Moake, et al., *New Eng. J. Med.* 307: 1432, 1982; Moake, et al., JCI 78: 1456, 1986). Unusually large vWF multimers are also important in the adhesion of sickle red blood cells to human endothelial cells (Wick T. M., et al., *J. Clin. Invest.* 80: 905, 1987).

Fluid shear stress may reach very high levels, perhaps as high as 200 to 400 dynes per cm$^2$, in small arteries and arterioles that are partially occluded, as in atherosclerosis or vascular spasm. Under these conditions, vessels of the microcirculation are subject to thrombotic occlusion by aggregated blood platelets.

Administration of aurin tricarboxylic acid, triphenyl methyl dyes, substituted naphthalene sulfonic acid deviatives or small organic molecules with high negative charge densities, or the analogues or agonists of these compounds, may prevent the vWF-mediated aggregation or agglutination of platelets and, thereby, prevent the formation of thromboemboli. These compounds may interfere with vWF-mediated sickle red cell-endothelial cell interaction and, thereby ameliorate, prevent or reverse sickle cell crises. Because of their capacity to interfere with vWF-mediated platelet clumping or adhesion of platelet tumor-cell clumps to the blood vessel wall, the compounds may inhibit the formation of tumor cell metastases. By the same mechanism, they may also slow the aging process.

Therefore, administration of one of the compounds useful in the present invention to an individual with a narrowed arterial lumen due to atherosclerosis, vasospasm or a combination of both, should prevent the vWF-mediated agglutination or aggregation of platelets and the ensuing formation of thromboemboli and vascular occlusion. Such conditions of narrowed arterial lumena include, but are not limited to, coronary and cerebral atherosclerosis. Similarly, after individuals have undergone procedures for recanalization of native, grafted or synthetic vessels, the administration of such a compound to prevent reocclusion of said vessel by platelet thrombi would be beneficial. Such procedures for recanalization include, but are not limited to: the surgical placement of a graft of arterial, venous or synthetic origin; the use of mechanical agents such as balloon catheters or laser light to disrupt vascular occlusions; the surgical removal of thromboemboli from the vascular lumen; or the use of chemical agents such as enzymes (e.g., streptokinase or urokinase) or enzyme activators (e.g., tissue plasminogen activator) for the purpose of dissolving thromboemboli.

These compounds may be useful in treating sickle cell disease to prevent or ameliorate the vWF-mediated adhesion of red blood cells and platelets to vessel walls with the subsequent vascular occlusion and painful ischemic crises.

These compounds may also be administered to individuals with malignancies in order to decrease the frequency of successful metastatic implants of tumor cells at sites remote from the primary tumor, due to the dependence of the malignant cells on platelets and vWF for attachment, implanatation and subsequent growth.

Individuals with atherosclerosis may benefit from the administraion of the compounds of the present invention by a decrease in the attachment of platelets to the damaged vascular endothelium with the attendant release of growth factors and chemoattractants that accelerate the atherosclerotic and aging processes.

The compounds useful in practicing the present invention are selected from, but not limited to, the group of compounds having the general formulas:

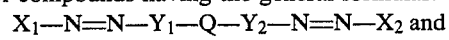

and

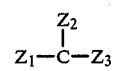

wherein
$X_1$ and $X_2$ are

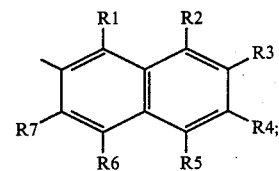

$Y_1$ and $Y_2$ are

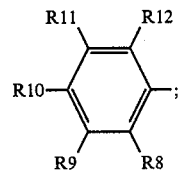

$Z_1$, $Z_2$ and $Z_3$ are benzyl groups substituted in one or more positions with hydrogen groups, carboxyl groups or hydroxyl groups;

Q is a bond between the adjacent aryl or substituted aryl groups or a ureylene group or an alkylene or substituted alkylene group; and $R_1$–$R_7$ can be hydrogen or a substituent such as hydroxyl groups, amino groups, sulfate groups, phosphate groups, nitrate groups, nitrite groups, carboxyl groups, ester groups, ether groups, or alkyl groups or salts of the aforementioned acidic substituents, e.g., SO$_3$Na, COONa, or the like; and $R_8$–$R_{12}$ can be hydrogen, lower alkyl group, alkyl ether group or a lower alkanoyl oxy group.

The compounds particularly useful in practicing the present invention are selected from the group consisting of

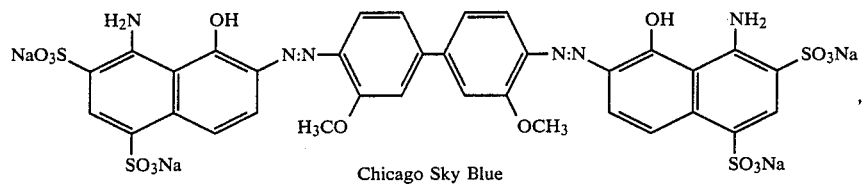
Chicago Sky Blue

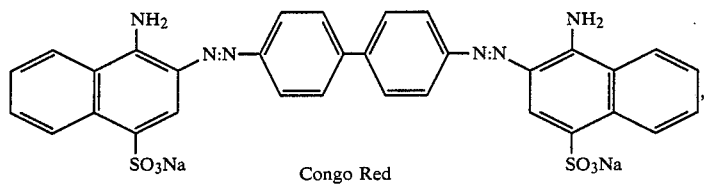
Congo Red

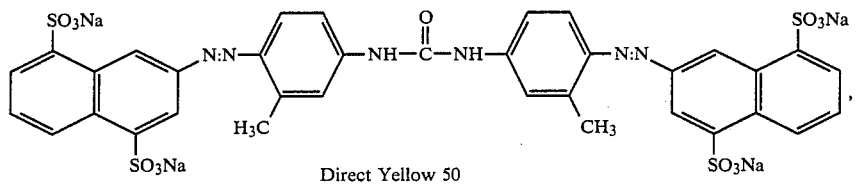
Direct Yellow 50

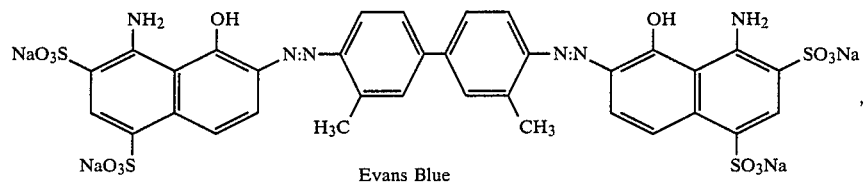
Evans Blue

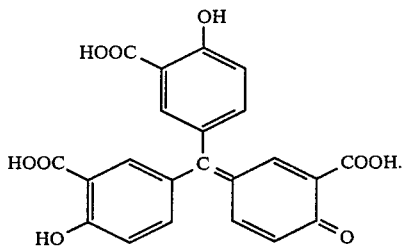
Aurin Tricarboxylic Acid

It is one object of the present invention to provide a treatment for thrombotic diseases that will interfere with the clumping of blood platelets in the arterial circulation, or attachment of blood platelets to the vessel wall.

Another object of the present invention is to prevent or impede the clumping of platelets in the presence of vWF multimers.

Another specific object of the present invention is to prevent clumping of platelets in the presence of large vWF multimers in acute, chronic relapsing and intermittent types of TTP and in the hemolytic uremic syndrome.

Another specific object of the present invention is to prevent adherence of red blood cells to vessel walls, directly or in association with platelets, in sickle cell disease and the acute crisis thereof.

Another specific object of the present invention was to provide a compound which would inhibit the clumping of blood platelets in the venous circulation.

Another object of the present invention was to provide acute and prophylactic treatment for arterial and venous thromboses, and sickle cell disease.

Another object of the present invention is to provide a treatment for pathological conditions resulting from arterial or venous occlusions. A more specific object is to provide a treatment for circulatory occlusions that will prevent ongoing aggregation of platelets, and cause de-aggregation.

Another object of the present invention is to provide a prophylactic treatment for the above mentioned pathological conditions that can be well tolerated by patients for long periods of time.

Another object of the present invention is to provide a prophylatic treatment for metastases of tumor cells and to delay certain aging phenomena.

Thus, in one embodiment, the present invention provides a method for preventing and treating thrombosis in an individual comprising administering a compound effective to inhibit the agglutination and aggregation of blood platelets to an individual in need of said treatment. In a preferred embodiment, the compound is selected from the group consisting of aurin tricarboxylic acid, triphenyl methyl dyes, substituted naphthalene sulfonic acid moieties, the analogs and agonists of these compounds and pharmaceutically acceptable salts thereof.

In another embodiment, the present invention provides a method for treating thrombosis in an individual comprising administering a compound effective to prevent further aggregation or agglutination of platelets, and to allow disaggregation of platelets to occur.

This treatment provides an ameliorating effect for diseases including arterial thrombotic disorders, venous thromboembolism, sickle cell anemia and cancer, as well as aging.

DESCRIPTION OF THE DRAWINGS

FIG. 5 demonstrates that the rate of platelet aggregation is proportional to the concentration of vWF and inversely proportional to the ATA concentration.

DESCRIPTION OF THE PREFERRED EMBODIMENTS

Figure 2:
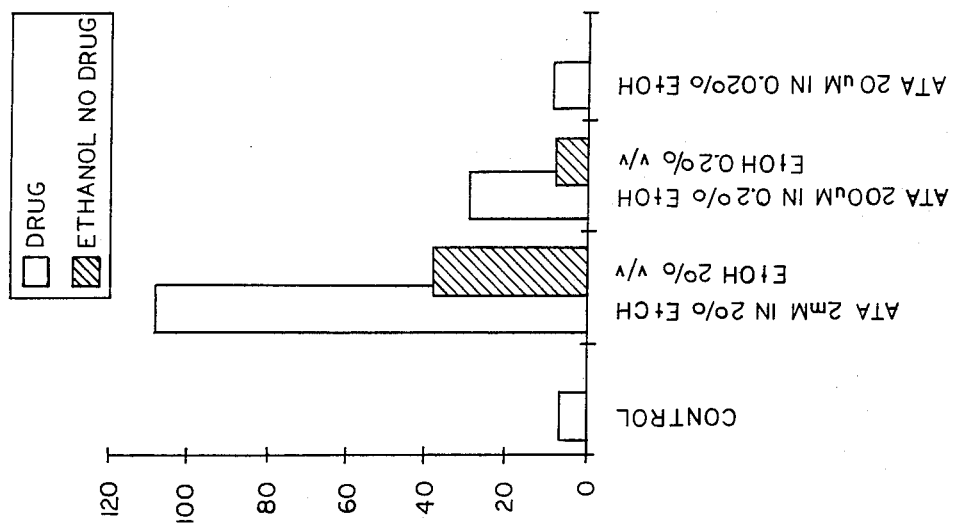
FIG. 2 demonstrates the concentration dependence of ATA-mediated inhibition of shear-induced platelet aggregation in PRP.

The method of the present invention is useful for the treatment of pathological conditions caused by the aggregation or agglutination of blood platelets. Typical pathological conditions caused by the aggregation of blood platelets include, but are not limited to, arterial thrombosis (including those involving coronary, cerebral and peripheral arteries and arterioles); venous thromboembolism; acute, chronic relapsing and intermittent types of TTP; HUS; acute crises in sickle cell disease; metastases in cancer; and aging.

The term "individual" is intended to include any animal, preferably a mammal, and most preferably, a human.

Compounds useful in the practice of the present invention include those compounds which inhibit the agglutination or aggregation of platelets in the presence of vWF and/or collagen, as well as those compounds which cause platelet clumps in the presence of vWF and/or collagen to disassociate or disaggregate. Compounds which prevent the binding of vWF to platelets will also be useful in the practice of the present invention.

The terms "platelet aggregation" and "platelet agglutination" are meant to include the formation of clumps of platelets mediated at least partially by the attachment of vWF multimers to platelet surface glycoproteins Ib, IIb-IIIa, or other surface receptors.

The compounds useful in practicing the present invention are selected from, but not limited to, the group of compounds having the general formulas:

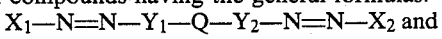

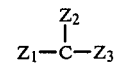

wherein
$X_1$ and $X_2$ are

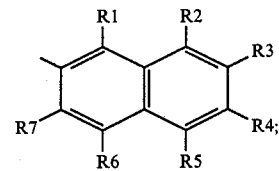

$Y_1$ and $Y_2$ are

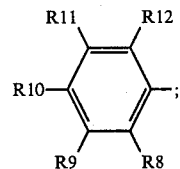

$Z_1$, $Z_2$ and $Z_3$ are benzyl groups substituted in one or more positions with hydrogen groups, carboxyl groups or hydroxyl groups;

Q is a bond between the adjacent aryl or substituted aryl groups or a ureylene group or alkylene or substituted alkylene groups; and $R_1$-$R_7$ can be hydrogen or a substituent such as hydroxyl groups, amino groups, sulfate groups, phosphate groups, nitrate groups, nitrite groups, caboxyl groups, ester groups, ether groups, or alkyl groups or salts of the aforemention acidic substituents, e.g., $SO_3Na$, $COONa$, or the like;

$R_8$–$R_{12}$ can be hydrogen, a lower alkyl group, alkyl ether group or a lower alkanoyl oxy group.

The compounds particularly useful in practicing the present invention are selected from the group consisting of red-orange powder that is sparingly soluble in water but soluble in ethanol. It is tightly protein bound when in solutions containing proteins, such as blood plasma. The molecular weight is 422.35.

Among the analogs of aurin tricarboxylic acid which may be useful in the method of the present invention include, but are not limited to, aurin dicarboxylic acid and aurin monocarboxylic acid, crystal violet, and gentian violet. Additionally, aurin may be substituted with

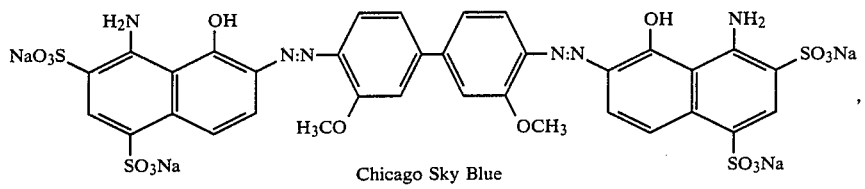
Chicago Sky Blue

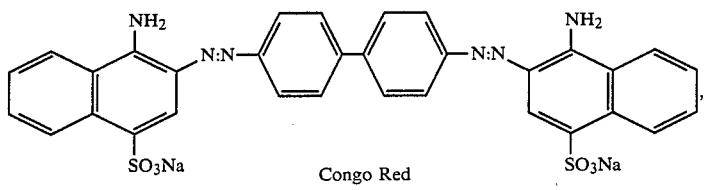
Congo Red

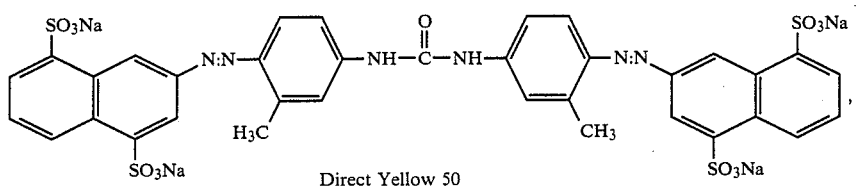
Direct Yellow 50

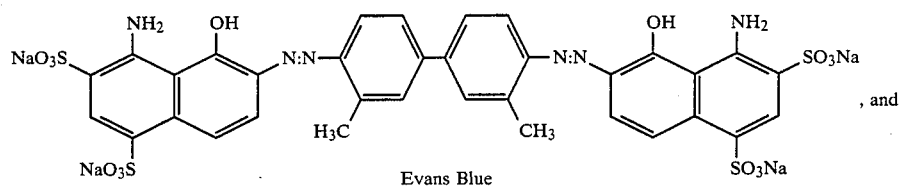
Evans Blue, and

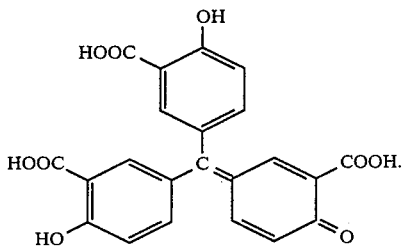
Aurin Tricarboxylic Acid

The compounds useful in the present invention, which act to impair platelet aggregation or agglutination in the presence of vWF multimers include, but are not limited to, aurin tricarboxylic acid, triphenyl methyl dyes, substituted naphthalene sulfonic acid moieties, small organic molecules with high negative charge densities, their analogs and agonists. Preferably, aurin tricarboxylic acid (ATA), Direct Yellow 50 (DY50), Congo Red (CR), Chicago Sky Blue (CSB) and Evans Blue (EB) are used.

Aurin tricarboxylic acid (ATA) is comprised of three phenolic rings, each substituted with a carboxylic acid moiety, all attached to a central carbon atom. It is a one or more acidic moieties other than carboxylate. Examples include, but are not limited to, phosphate, sulfonate and nitrates.

Typical aurin tricarboxylic acid agonists are compounds which demonstrate the biological activities substantially similar to that of aurin tricarboxylic acid. Aurin tricarboxylic acid agonists include compounds which prevent the aggregation or agglutination of platelets in the presence of vWF, or disaggregate platelets which have aggregated in the presence of vWF.

Typical aurin tricarboxylic acid agonists include, but are not limited to, compounds such as Evans Blue dye, Congo red, Direct Yellow 50, Chicago Sky Blue and other substituted naphthalene sulfonic acid dyes. Substituted naphthalene sulfonic acid dyes include compounds which contain naphthalene mono- or poly-sulfonic acid moieties which may be substituted further at the remaining positions. Furthermore, two or more napthalene sulfonic acid moieties may be joined into one molecule via an azo linkage or other chemical linkage. Other agonists include benzidine dyes of the disazo type with the structure:

wherein $A_1$ and $A_2$ are substituted naphthalene sulfonic acid moieties, and the diphenylene moiety can be unsubstituted or substituted with lower alkyl groups, alkyl ether groups or lower alkenoyl oxy groups. Examples include Diamine Green B and Acid Anthrocene Red G. When A and $A_2$ are substituted with 4-amino-1-naphthalene sulfonic acid and the diphenylene moieties are unsubstituted, the compound is Congo Red.

A suitable screening method for determining whether a given compound is an agonist or analog of aurin tricarboxylic acid, the triphenylmethyl dyes or substituted naphthalene sulfonic acid dyes suitable for practicing the present invention comprises measuring the inhibition of the aggregation or agglutination of blood platelets in vitro in the presence of vWF multimers by the technique described in detail in Example 7. The fluid shear stress applied to a platelet suspension in a viscometer provides a model for the shear stresses on platelets in flowing blood in stenotic arteries and arterioles. Briefly, a shear stress is applied to platelets in the presence of large vWF multimeric forms and the rate of aggregate formation is measured in an aggregometer or particle counter. The test compound is added during the incubation and the degree of inhibition of aggregation is determined. Any compound which inhibits aggregation by at least 30% is considered adequate for use in the practice of the present invention.

Another embodiment of the present invention is the inhibition of collagen activation of platelets. vWF enhances the rate of collagen-platelet aggregation. The rate and extent of collagen-induced platelet aggregation is reduced by the presence of ATA in the reaction medium. By preventing vWF attachment to the platelet surface, ATA and the other compounds useful in the present invention may curtail the availability of platelet collagen binding sites. ATA may also interfere with the binding of collagen to its platelet surface receptor.

In another embodiment, the invention comprises a method for preventing further aggregation of blood platelets by administration of the compounds identified above as useful in practicing the invention. Since individuals suffering from conditions such as arterial thrombosis, venous thromboembolism and sickle cell crisis may have platelet aggregates present in the body prior to seeking medical attention, the administration of the compounds of interest may be utilized to prevent further blood platelet aggregation. Such treatment will also enhance the natural in vivo platelet disaggregating mechanism by preventing further platelet aggregation, preventing addition of new platelets to an already formed aggregate and by reversing the aggregation of the platelet clumps.

Administration of the compounds useful in the method of the present invention may be by topical, parenteral, oral, intranasal, intravenous, intramuscular, subdermal, or any other suitable means. The dosage administered may be dependent upon the age, weight, kind of concurrent treatment, if any, and nature of the pathological condition associated with the development of platelet aggregation or agglutination, as well as the stage of the pathological dysfunction. The effective compound useful in the method of the present invention may be employed in capsules, tablets, liquid solutions, suspensions or elixirs for oral administration, or sterile liquid solutions, suspensions or emulsions for parenteral injection. Any inert carrier is preferably used (e.g., saline or phosphate-buffered saline), or any such carrier in which the compounds used in the method of the present invention have suitable solubility properties for use in the method of the present invention.

The minimum possible amount of drug should be administered in any particular situation. The dosage of drug administered will vary between individuals based on body weight, metabolic factors, serum protein concentrations, and the serum concentration of other pharmaceutical substances in the recipient. Typically for ATA a concentration of 400 micromoles per liter of plasma is desirable, or for a hypothetical 70 Kg person with 3 liters of plasma, 0.5 grams of active drug would be administered. The frequency of administration varies dependent on the same factors mentioned, but typically it is daily or several times per day.

Having now generally described the invention, the same may be further understood by reference to the following examples, which are not intended to be limiting unless so expressly stated.

EXAMPLE 1

PRODUCTION OF VON WILLEBRAND FACTOR vWF is a glycoprotein multimer that mediates platelet-platelet, platelet-vessel wall and sickle red-blood-cell to vessel wall adhesion. von Willebrand factor (vWF) was prepared for use in the assay systems described below from several source materials. Purification of human plasma type vWF multimeric forms was carried out from blood bank cryoprecipitate and fractionated as described in Moake, et al., JCI 78: 1456, 1986, incorporated herein by reference.

Unusually large vWF multimers were prepared from human umbilical vein endothelial cell cultures.

In order to prepare the endothelial cell cultures, fresh umbilical cords were obtained and the umbilical veins were canulated and rinsed with 100 ml of sterile, 37° C., phosphate buffer (0.14M NaCl, 0.0004M KCl, 0.011M glucose, 0.00022M $NaH_2PO_4$, and 0.0081M $Na_2HPO_4$). The veins were filled with collagenase (12 ml dissolved in 50 ml of 37° C. phosphate-buffered saline (PBS; containing 0.0027M KCl, 0.0015M $KH_2PO_4$, 0.137M NaCl, 0.0081M $Na_2HPO_2.7H_2O$, and 0.00049M $MgCl_2$)). After incubation for 30 min the collagenase suspensions were collected, and the veins rinsed with 100 ml of phosphate buffer to ensure collection of all cells. The effluent was centrifuged for 10 min at 100×g and the cell pellets were resuspended in complete medium. Growth medium consisted of medium 199 with 20% heat-inactivated fetal calf serum (complete medium 199), 0.10 mg/ml penicillin and streptomycin, 0.20 mg/ml neomycin, and 0.292 mg/ml glutamine. Cells were seeded on to culture dishes coated with gelatin or collagen to improve surface properties and the cells were grown to confluence in a 37° C. incubator in a humidified atmosphere of 5% $CO_2$ in air. Subsequently, the confluent endothelial cell cultures were rinsed in PBS, and incubated at 37° C. for 48 hrs in serum-free medium (SFM) and the endothelial cell supernatants were collected. SFM consisted of medium 199 supplemented with 5.0 mg/ml bovine insulin, 5.0 mg/ml human transferin, 0.4% human albumin, 0.10 mg/ml penicillin and streptomycin, 0.20 mg/ml neomycin, and 0.292 mg/ml glutamine. The supernatant, when removed, contained vWF antigen ranging from 2.8 to 11 units/dl. vWF multimeric analysis by SDS-1% agarose gel electrophoresis and autoradiography revealed the presence of multimeric forms substantially larger than those found in normal human plasma. Normal platelet-poor plasma contains 100 units/dl of vWF antigen.

EXAMPLE 2

PREPARATION OF RED BLOOD CELLS FOR ADHESION EXPERIMENTS

Red cell suspensions were prepared by drawing the blood into sodium heparin (14.3 USP units/ml), centrifuging at 100×g for 10 min, and collecting the red blood cells. The red blood cells were washed 3 times in SFM and resuspended in either SFM, endothelial cell supernatant, or endothelial supernatant depleted of vWF by incubation with rabbit anti-human vWF antibody linked to protein A-Sepharose CL-4B.

EXAMPLE 3

ASSAY FOR ADHESION OF RED BLOOD CELLS TO ENDOTHELIAL CELL MONOLAYERS

The adhesion assay was performed utilizing confluent endothelial monolayers on glass slides as the base of a modified Richardson flow chamber held in place by an applied vacuum. The chamber was mounted on a stage of an inverted, phase-contrast microscope and maintained at 37° C.

The endothelial cell monolayer was rinsed for 5 min with SFM at a constant flow rate of 0.0764 ml/min generated by a Harvard syringe pump producing a wash shear stress of 1.0 dyne/$cm^2$. (A shear stress typically found in the venules.) The red cell suspension was then passed over the endothelial cell monolayer for 10 min. The endothelial cell monolayer was then rised for 20 min with SFM to remove nonadherent red cells. The number of adherent cells was counted in random fields ranging over the entire slide.

EXAMPLE 4

IRMA PROCEDURE FOR vWF ANTIGEN DETERMINATION

Determination of the levels of vWF antigens was performed by solid phase immunoradiometric assay (IRMA) using rabbit anti-human vWF IgG and rabbit [$^{125}$I]-anti-human vWF IgG as described by Counts, Br. J. Haematol, 31: 429, 1975.

EXAMPLE 5

PREPARATION OF PLATELETS

Blood was obtained from volunteer donors who had not ingested aspirin or other medications for three weeks prior to donation. For platelet rich plasma (PRP), blood was drawn into plastic syringes containing one part in six 3.8% Sodium Citrate. PRP was made by centrifugation of blood at 400×g for 15 minutes.

Washed platelets were prepared from blood drawn into acid-citrate-dextrose (0.65M citric acid, 0.085M sodium citrate, 0.111M dextrose), pH 4.5. PRP was obtained by gentle centrifugation of the blood. Platelets were sedimented at 1000×g for 15 minutes, washed in 10 mM HEPES buffer, pH 6.9, containing heparin (10 U/ml) and apyrase (2.5 U/ml), and resuspended in 10 mM HEPES buffer, pH 7.4. Platelet suspensions used for shear experiments contained glucose bovine serum albumin and $CaCl_2$ at final concentrations of 100 mg/dl, 0.35 g/dl and 1 mM, respectively. The platelets were formaldehyde-fixed by a modification of the procedure of Zaleski and Olson (in press). Briefly, the platelets were treated in vitro with 55 mM aspirin (ASA), gently rotated for 30 min. at 25° C., washed in citrated saline (150 mM NaCl, 6 mM trisodium citrate, 0.9 mM disodium EDTA, pH=7.1), incubated with 1% paraformaldehyde at 25° C. for 2 hours, washed three more times, and stored at −70° C. They were tested periodically to ensure that they remained fully functional in ristocetin cofactor assays wherein formaldehyde fixed platelets (200,000/$\mu$l) are mixed with normal platelet-poor plasma diluted as a source of vWF. The mixture is placed in an aggregometer and ristocetin (1 mg/ml) is added. Functional activity is defined as an increase in the light transmission as the platelets form large clumps that disperse less incident light than individual platelets in suspension.

EXAMPLE 6

THE VISCOMETER AS A MEANS OF APPLYING SHEAR STRESS TO PLATELET SUSPENSIONS

One in vitro system used to test the effectiveness of compounds in practicing the present invention utilized the inhibition of platelet aggregation induced by shear stress in the presence of vWF. In order to apply a measured shear stress, a Ferranti Model 781 (Ferranti Electric, Inc., Commack, NY) cone and plate viscometer as described in detail previously and in Example 3 was used. (Moake, et al., *J. Clin. Invest.* 78: 1456 (1986)) Samples (0.6 ml), with or without drug, containing fresh platelets (unwashed or washed) prepared as in Example 5, and a source of vWF multimers (prepared as described in Example 1 from normal plasma; the largest plasma-type vWF forms purified from the cryoprecipitate fraction of normal plasma prepared as described in Example 1; or human umbilical vein endothelial cell supernatant containing unusually large vWF multimers, i.e., vWF multimeric forms larger than those found in normal human plasma, prepared as described in Example 1) were applied to the plate. 10 $\mu$l samples were taken for particle counting. A shear force of 180 dynes/$cm^2$ for platelet rich plasma (PRP) and 120 dynes/$cm^2$ for washed platelet suspensions was applied for 30 seconds. Particle counts were again performed. 10 $\mu$l samples, diluted in 20 ml of Isoton II containing 0.5% glutaraldehyde, were counted on the Coulter ZBI Electronic Particle Counter and Channelzyer using a 50 mM aperture. Particles with sizes ±20% of the mean platelet distribution in the unsheared samples were considered as single platelets. The disappearance of single platelets could be accounted for by the formation of platelet aggregates. Thus, the percent decrease in single platelets was directly related to the percent increase in platelet aggregates. All counts were done in duplicate.

EXAMPLE 7

ASSESSMENT OF PLATELET AGGREGATION

Platelet aggregation or agglutination was measured with a Bio-Data Model PAP-2 aggregometer. The reaction volume was 500 μl. In experiments using fresh platelets, 400 μl of PRP was added to a siliconized glass cuvette, and 50 μl of buffer or drug was added. A magnetic stir bar was placed in the cuvette and a stable baseline light transmission achieved. 50 μl of an aggregating agent (ristocetin, ADP, collagen or arachidonic acid) was added. The blank was composed of 300 μl of PRP and 200 μl of buffer. In experiments with formaldehyde fixed platelets, 350 μl of platelets in 10 mM HEPES buffer, pH 7.4, with platelet counts specified for each experiment were placed in the cuvette. 50 μl of vWF (purified large plasma-type vWF multimers of endothelial cell supernatant concentrations as specified for each experiment) were added, along with 50 μl of drug or buffer. The aggregating agent was added as in the PRP experiments described in Example 7. The initial rate and extent of changes in light transmission were recorded.

An alternative method for measuring aggregation or agglutination was used to analyze compounds which could not be used in the aggregometer because of their optical properties, or to follow the disappearance of vWF from the reaction medium. Briefly, 400 μl of formaldehyde-fixed platelets were placed in a test tube and 50 μl of purified plasma-type vWF multimers were added for a final vWF concentration of 20 U/dl. Either 50 μl of drug or buffer was added, and 10 μl samples were taken for particle counting. 100 μl of the mixture were put in a plastic microfuge tube, the platelets were sedimented at 10,000×g, and the supernatant saved for vWF antigen quantification and multimeric analysis. To the remaining platelet-vWF suspension, 50 μl of ristocetin was added for a final concentration of 1 mg/ml, and the reaction mixture was placed on a rotating shaker table for 3 minutes at 25° C. 10 μl samples were again taken for particle counting. The remaining sample was placed in a microfuge tube, the platelets pelleted by centrifugation, and the supernatant again stored for vWF quantification and multimeric analysis. vWF antigen was quantified by immunoradiometric assay. vWF multimeric patterns were analyzed by sodium dodecyl sulfate (SDS)-1% agarose gel electrophoresis, overlaid with $^{125}$I-labelled polyclonal rabbit anti-human vWF IgG, and the development of autoradiograms at −70° C. for 24–72 hours.

EXAMPLE 8

Testing of Compounds For The Ability To Block Platelet Aggregation

Figure 1:
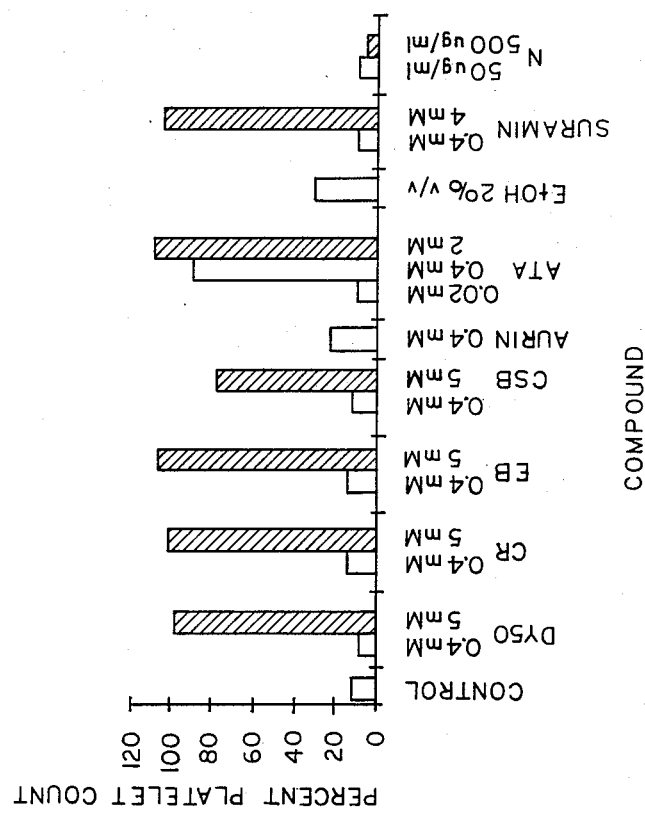
FIG. 1 demonstrates the effects of DY50, CR, Eb, CSB, aurin, ATA, suramin and vancomycin on shear-induced platelet aggregation in normal platelet-rich plasma (PRP).

All compounds were first screened for their ability to block platelet aggregation in PRP in the shear field as described in Example 6. As demonstrated in FIG. 1, at low concentrations (200–400 μM) only ATA showed anti-aggregation activity. There was modest interdonor variability in the degree of inhibition of vWF mediated shear-induced aggregation below this concentration, suggesting that in plasma the threshhold of activity is approximately 200 μM. DY50, CR, CSB, and EB exhibited no inhibitory activity at 0.4 mM. Since ATA was dissolved in ethanol, a control of 2% EtOH which was equivalent to the ETOH concentration in the 2 mM ATA sample was also tested and showed some minimal inhibitory effects. At higher concentrations, ATA (2 mM), suramin (4 mM), and CSB, EB, DY50 and CR (all 5 mM) showed inhibitory activity. In other platelet aggregation studies using ristocetin, ADP, collagen and arachidonic acid, 4 mM suramin was toxic to platelets causing disruption of platelet metabolism. The dyes do not affect ADP-mediated aggregation.

Figure 3:
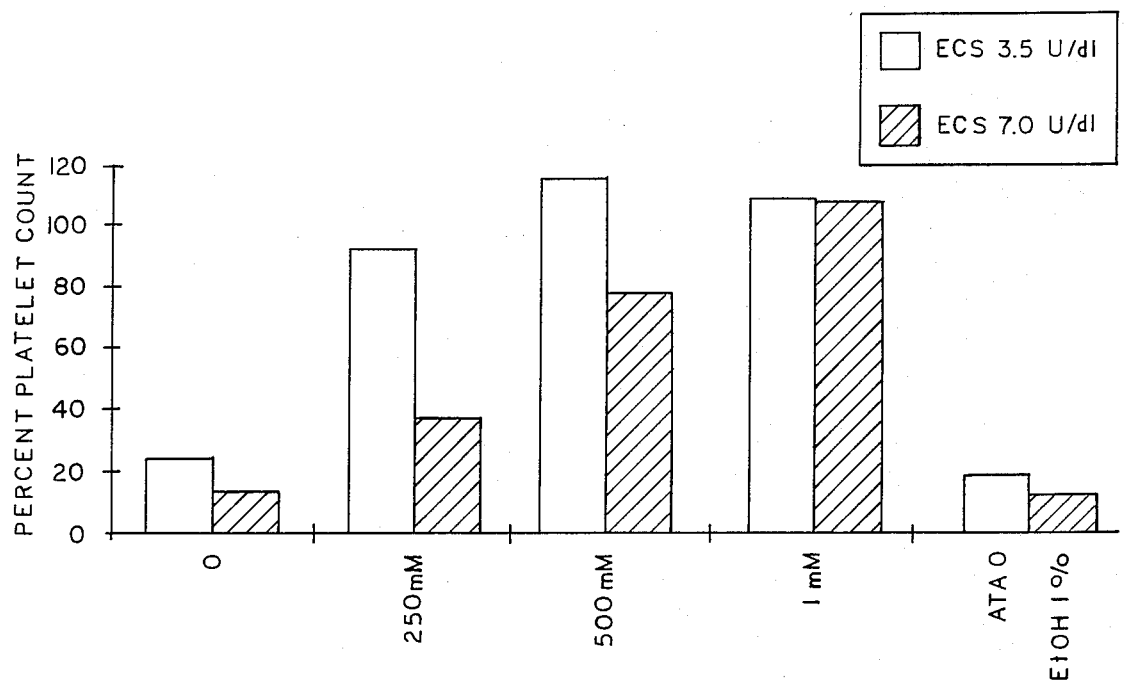
FIG. 3 demonstrates that the shear-induced aggregation of fresh, washed platelets suspended in buffer utilizing endothelial cell supernatants (ECS) containing unusually large vWF multimers is inversely proportional to the concentration of ATA, and proportional to the concentration of vWF.

Vancomycin, which has been shown to interfere with ristocetin-induced platelet aggregation, had no effect on shear-induced platelet aggregation at concentrations up to ten times the expected therapeutic concentration in PRP. There was a direct relationship between the concentration of ATA and its ability to block shear-induced platelet aggregation as demonstrated in FIG. 2. The ethanol solvent had only modest platelet inhibitory activity. At a given concentration of ATA, the degree of inhibition of platelet aggregation was inversely proportional to the concentration of vWF, as shown in FIG. 3.

Figures 4A, 4B:
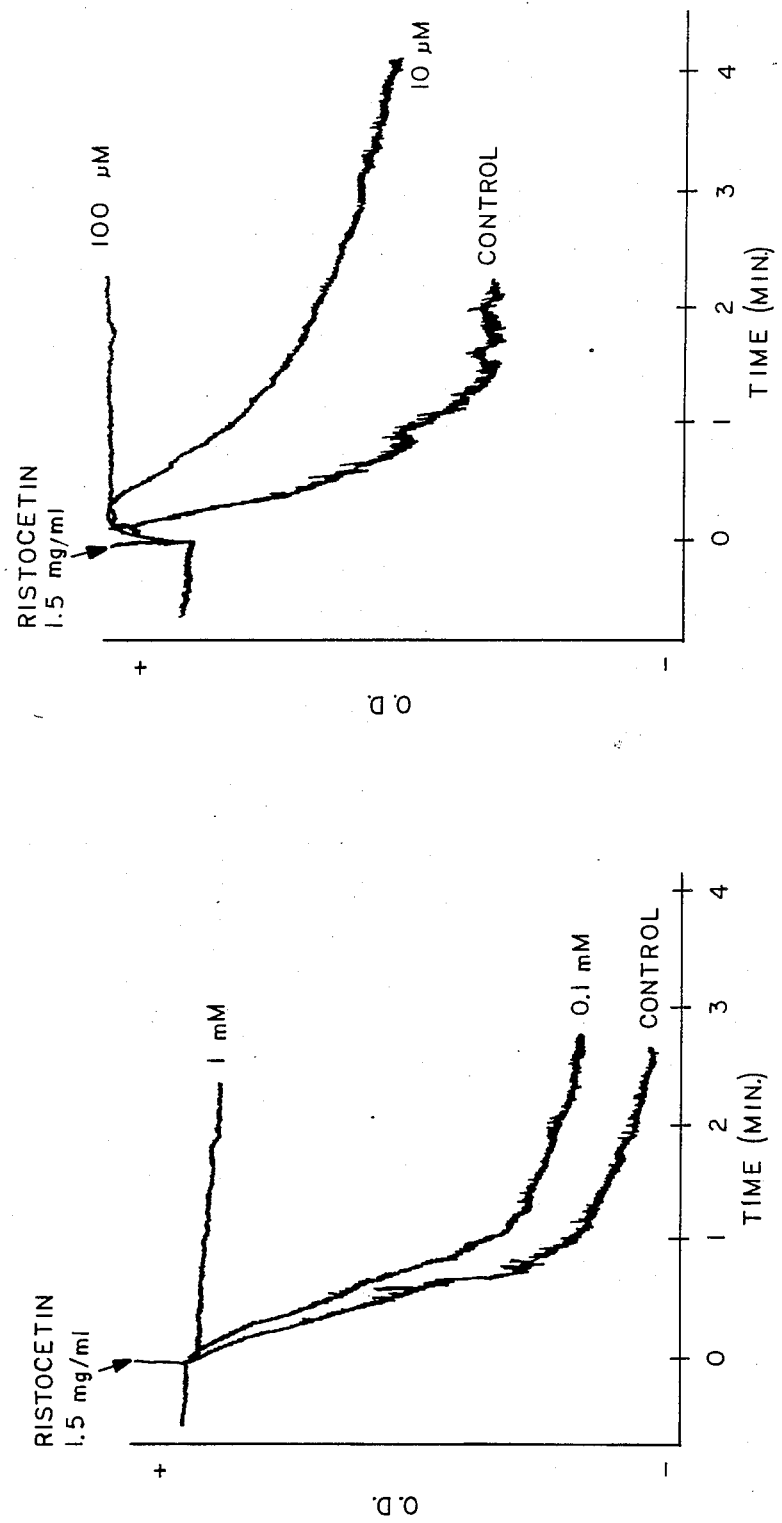
FIG. 4 demonstrates that ATA inhibits ristocetin-induced PRP (4a) and fixed platelet aggregation (4b) in a dose-dependent manner.
Figure 5A:
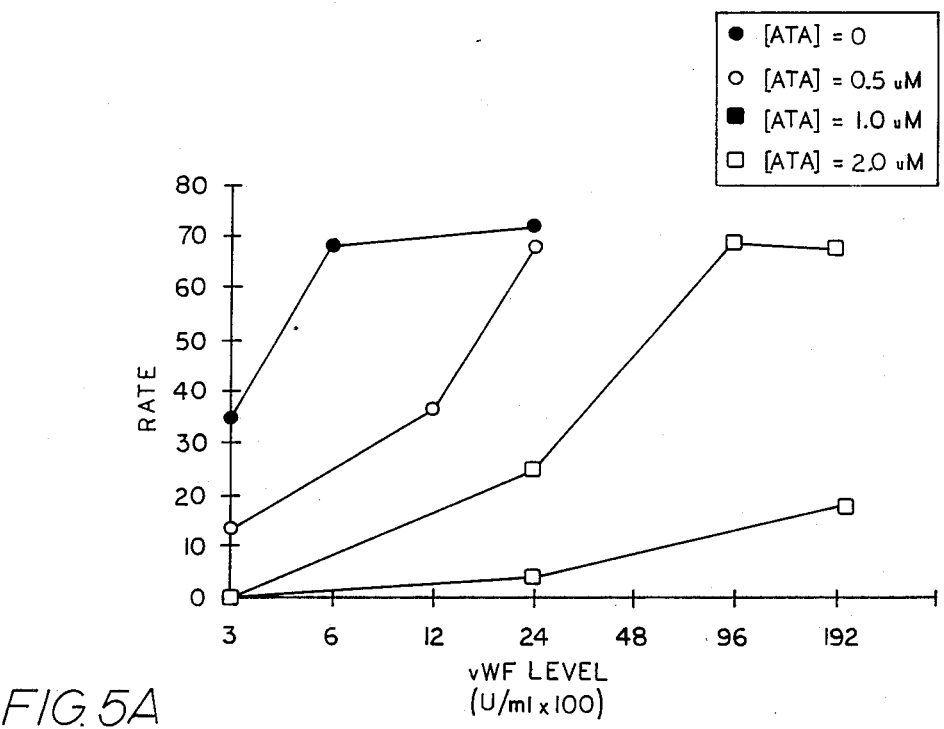
FIG. 5a is a linear plot of the rate of aggregation versus the dose of vWF.
Figure 5B:
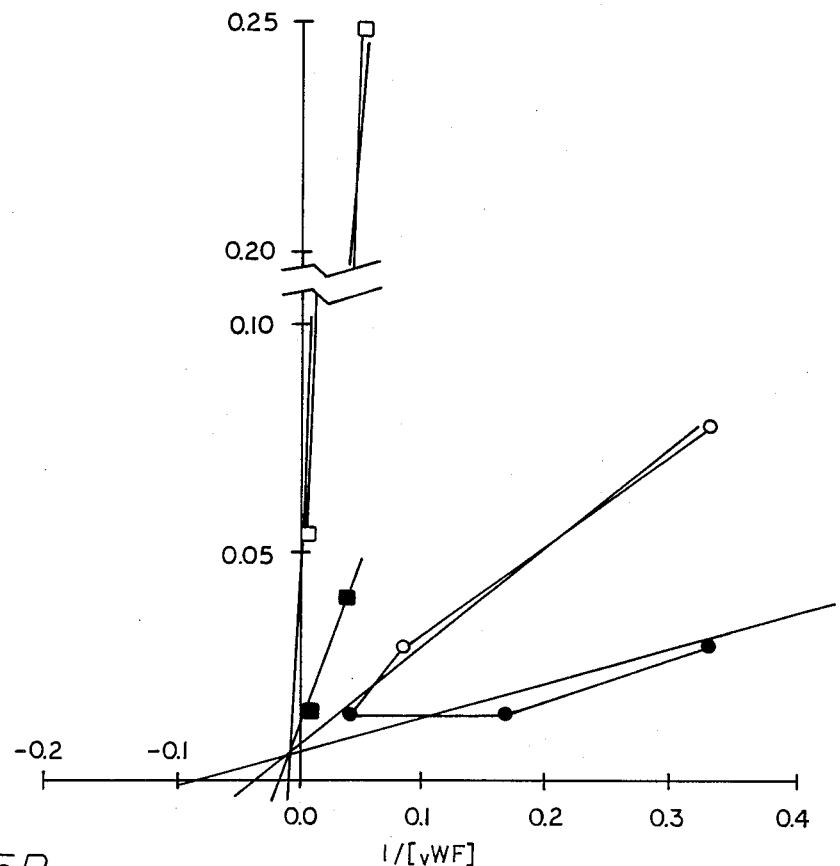
FIG. 5b is a double reciprocal plot of the data shown in FIG. 5a demonstrating a constant $V_{max}$ at all concentrations of ATA.

Platelet aggregometry, as described in Example 7, showed that ATA effects events which are probably mediated through the platelet glycoprotein Ib receptor, but does not effect platelet activation and clumping induced by aggregating agents that have different mechanisms of action requiring platelet metabolism. Ristocetin-induced aggregation or agglutination (Moake, et al., Blood, 50: 397, 1977) was inhibited in a concentration dependent fashion by ATA in both fresh PRP (FIG. 4a) or formaldehyde-fixed platelet systems (FIG. 4b). When platelets were suspended in plasma (i.e., PRP), as compared to buffer and a source of vWF, approximately 1000-fold greater concentrations of ATA were needed to achieve the same degree of inhibition of platelet aggregation due to the binding of ATA by plasma proteins. The competition between ATA and vWF observed in the shear-induced platelet aggregation system was also seen in ristocetin-mediated aggregation of formaldehyde-fixed platelets, as demonstrated on FIG. 5. The inhibition of vWF-platelet binding by ATA follows classical first-order kinetics. A double reciprocal plot of the data presented in FIG. 5 shows that the $V_{max}$ of platelet aggregation is unchanged and the $K_m$ of platelets for vWF increases proportionally with the concentration of ATA in the system as demonstrated on FIG. 5a.

Figure 6:
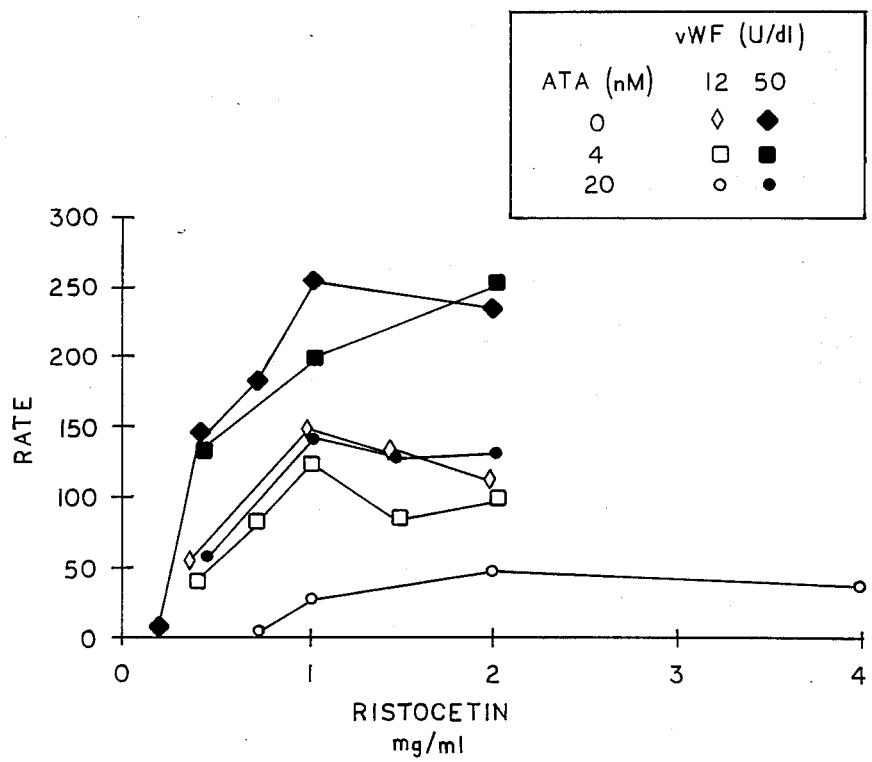
FIG. 6 demonstrates that increasing the concentration of ristocetin above a final concentration of 1 mg/ml does not affect the rate of platelet aggregation, which is dependent on the concentration of vWF and ATA.
Figure 7:
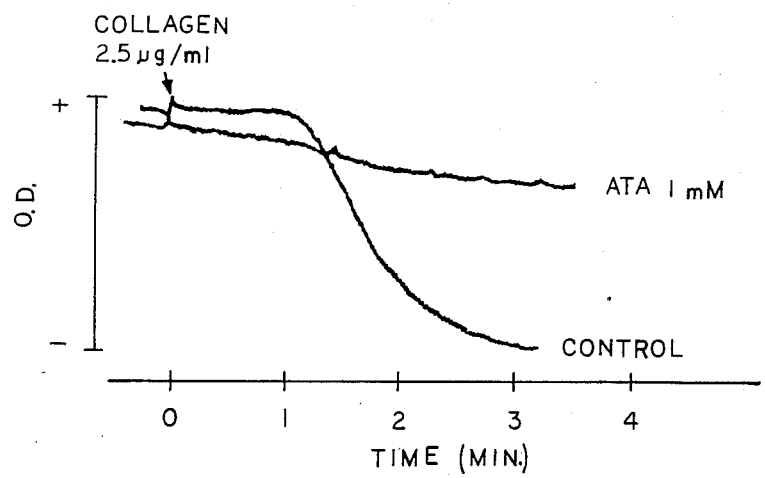
FIG. 7 demonstrates that ATA causes inhibition of collagen-induced aggregation of platelets in fresh normal PRP.
Figure 8:
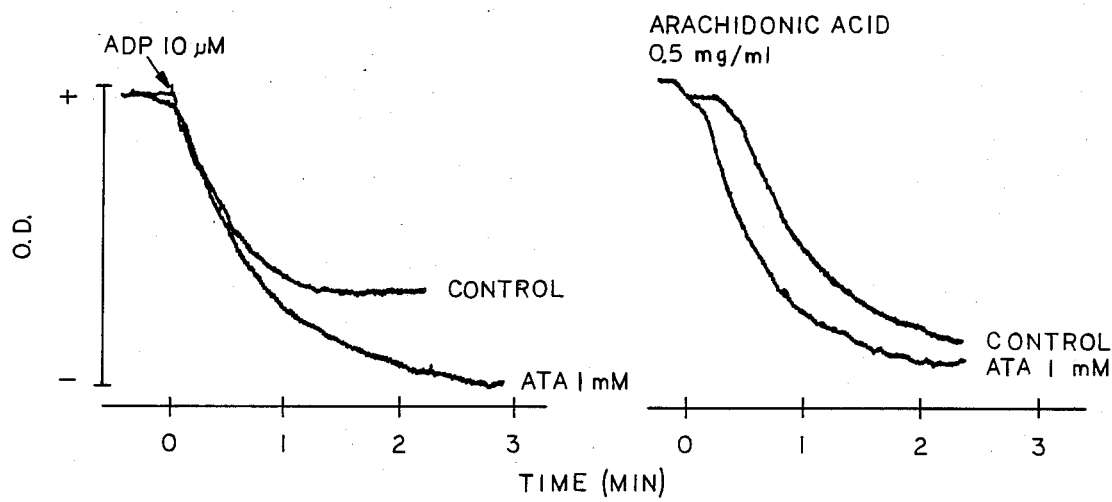
FIG. 8 demonstrates that ADP and arachidonic acid-mediated aggregation of platelets in fresh normal PRP is not inhibited by ATA.

Formaldehyde fixed platelets (300,000 ml) were mixed with 1 mg/ml ristocetin, purified plasma-type vWf and ATA in the aggregometer as described in Example 7. The rate of aggregation was determined by plotting the initial light transmission against time. Ristocetin is not rate limiting above a threshold concentration of 1 mg/ml (FIG. 6). Collagen-induced platelet aggregation in PRP is partially inhibited by the addition of ATA, as demonstrated on FIG. 7, while ADP and archidonic acid-mediated platelet aggregation in fresh PRP are unaffected by the addition of ATA (FIG. 8).

Figure 9:
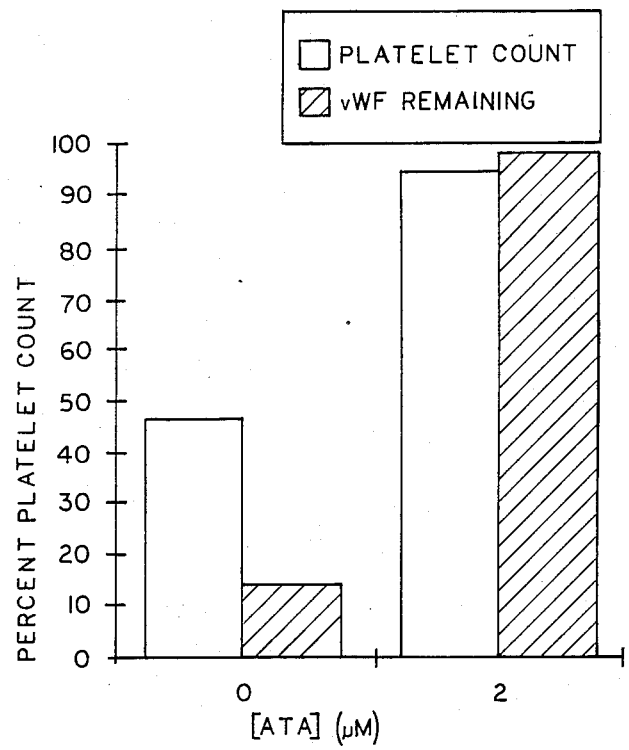
FIG. 9 demonstrates that ATA blocks ristocetin-mediated agglutination of fixed platelets and prevents consumption of vWF antigen from the reaction medium.
Figure 10:
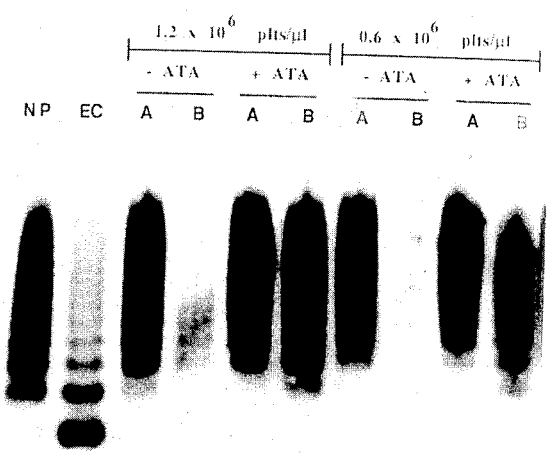
FIG. 10 shows an SDS-1% agarose gel electrophoretogram of the supernatant of a mixture of formaldehyde-fixed platelets, purified plasma-type vWF multimers, ATA or buffer, and ristocetin. After electrophoresis, the gel was overlayed with $^{125}$I rabbit anti-human vWF, IgG, and the autoradiogram developed. NP is normal plasma; and EC is endothelial cell supernatant containing unusually large vWF multimers. Lane A shows unagglutinated samples prior to the addition of ristocetin; lane B shows samples after ristocetin-addition and platelet agglutination.

The disappearance of vWF from the reaction medium as the platelets agglutinated was shown by reacting formaldehyde-fixed platelets (which have only glycoprotein IB available as a surface receptor), vWF and ristocetin on the shaker table as described in Example 7. When ATA was added, both agglutination of platelets and consumption of vWF were blocked as demonstrated in FIG. 9. The autoradiogram in FIG. 10 shows the disappearance of the largest vWF multimers purified from cryoprecipitate during platelet aggregation when ristocetin was absent. When ATA was added, both aggregation and vWF uptake were blocked. Thus, at least part of the effectiveness of ATA is due to inhibition of the interaction between vWF multimers and platelet surface glycoprotein Ib receptors.

Figure 11:
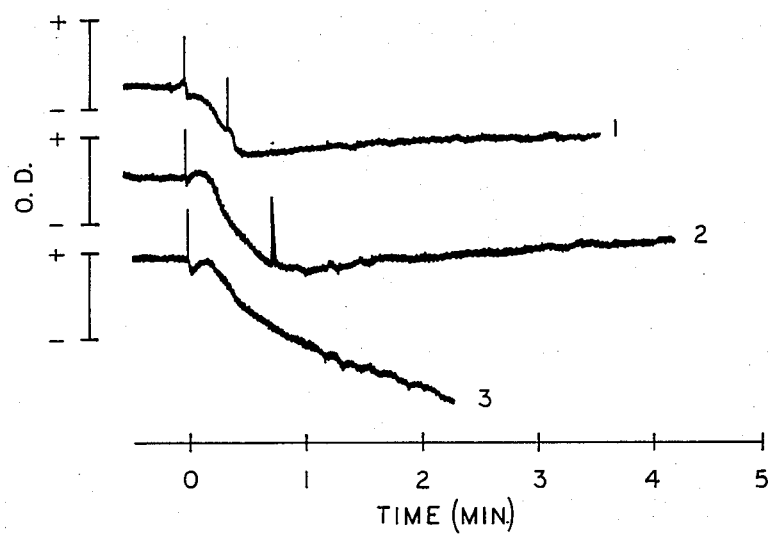
FIG. 11 demonstrates that ristocetin-induced platelet agglutination of formaldehyde-fixed platelets is blocked by the addition of ATA.

ATA does not reverse the ristocetin-induced aggregation of fresh platelets in PRP in the aggregometer. FIG. 11 demonstrates that the reaction is attenuated at any point by the addition of ATA, but no dissolution of formed platelet clumps occurs. This does not preclude the effectiveness of other mechanisms in vivo to dissolve platelet clumps in the presence of ATA.

By use of the simple in vitro assay discussed herein, one of skill in the art can by a simple preliminary trial in vitro ascertain quite quickly and routinely whether a chosen agent is useful in practicing the present invention.

Having now fully described the invention, it may readily be seen by those of skill in the art that the present invention can be performed utilizing equivalent agents without affecting the scope of the invention or any embodiment thereof.

What is claimed is:

1. A method for treating a condition in an individual comprising administering a compound in an amount effective to prevent aggregation of blood platelets to an individual in need of said treatment wherein said condition is selected from the group consisting of arterial thrombosis and venous thromboembolism and wherein said compound is selected from the group having the formulas.

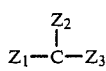

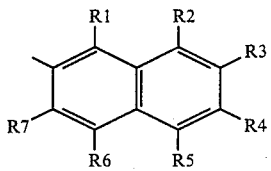

and salts thereof
wherein
$X_1$ and $X_2$ are

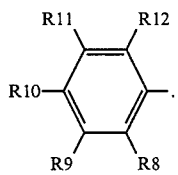

$Y_1$ and $Y_2$ are

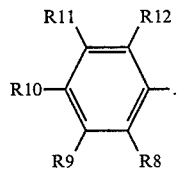

$Z_1$, $Z_2$ and $Z_3$ are benzyl groups substituted in one or more positions with hydrogen groups, carboxyl groups or hydroxyl groups, Q is a bond between the adjacent aryl or substituted aryl groups or a ureylene group or an alkylene or substituted alkylene group, and $R_1$-$R_7$ is selected from the group consisting of hydrogen, a hydroxyl group, an amino group, a sulfate group, a phosphate group, a nitrate group, a nitrite group, a carboxyl group, an ester group, an ether group, an alkyl group, and salts of the aforementioned acidic substituents; and $R_8$-$R_{12}$ is selected from the group consisting of hydrogen, a lower alkyl group, an alkyl ether group and a lower alkanoyl oxy group, and salts thereof.

2. A method for treating thrombosis in an individual comprising administering a compound in an amount effective to prevent aggregation of blood platelets to an individual in need of said treatment wherein said compound is selected from the group having the formulas $X_1$—N=N—$Y_1$—Q—$Y_2$—N=N—$X_2$ and

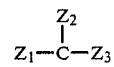

and salts thereof
wherein
$X_1$ and $X_2$ are

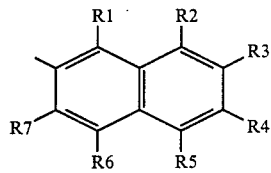

$Y_1$ and $Y_2$ are

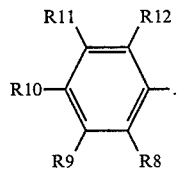

$Z_1$, $Z_2$ and $Z_3$ are benzyl groups substituted in one or more positions with hydrogen groups, carboxyl groups or hydroxyl groups, Q is a bond between the adjacent aryl or substituted aryl groups or a ureylene group or an alkylene or substituted alkylene group, and $R_1$-$R_7$ is selected from the group consisting of hydrogen, a hydroxyl group, an amino group, a sulfate group, a phosphate group, a nitrate group, a nitrite group, a carboxyl group, an ester group, an ether group, an alkyl group, and salts of the aforementioned acidic substituents; and $R_8$-$R_{12}$ is selected from the group consisting of hydrogen, a lower alkyl group, an alkyl ether group and a lower alkanoyl oxy group, and salts thereof.

3. The method of claims 1 or 2, wherein said compound is selected from the group having the formula $X_1$—N=N—$Y_1$—Q—$Y_2$—N=N—$X_2$ and salts thereof
wherein
$X_1$ and $X_2$ are

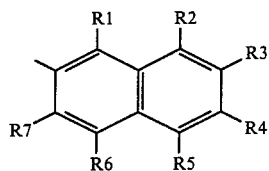

$Y_1$ and $Y_2$ are

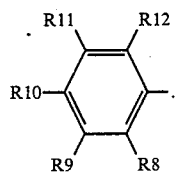

Q is a bond between the adjacent aryl or substituted aryl groups or a ureylene group or an alkylene or substituted alkylene group, and $R_1-R_7$ is selected from the group consisting of hydrogen, a hydroxyl group, an amino group, a sulfate group, a phosphate group, a nitrate group, a nitrite group, a carboxyl group, an ester group, an ether group, an alkyl group, and salts of the aforementioned acidic substituents; and $R_8-R_{12}$ is selected from the group consisting of hydrogen, a lower alkyl group, an alkyl ether group and a lower alkanoyl oxy group.

4. The method of claim 1 wherein said compound contains a substituted naphthalene sulfonic acid group.

5. The method of claim 1 wherein said compound is selected from the group consisting of aurin tricarboxylic acid, an analog of aurin tricarboxylic acid, and an agonist of aurin tricarboxylic acid.

6. The method of claim 1 wherein said compound is a triphenyl methyl dye.

7. The method of claim 1 wherein said compound is aurin tricarboxylic acid.

8. The method of claim 1 wherein said compound is Congo Red.

9. The method of any of claim 1 wherein said compound is Direct Yellow 50.

10. The method of claim 1 wherein said compound is Chicago Sky Blue.

11. The method of any of claim 1 wherein said compound is Evans Blue.

12. A method for dissociating platelet aggregates comprising administering a platelet aggregate disassociating amount of a compound selected from the group consisting of aurin tricarboxylic acid, analogs of aurin tricarboxylic acid, agonists of aurin tricarboxylic acid, triphenyl methyl dyes, analogs of triphenyl methyl dyes, agonists of triphenyl methyl dyes, and naphthalene sulfonic acid substituted compounds to an individual in need of said treatment.

13. The method of claims 1 or 2 wherein said compound is selected from the group having the formula

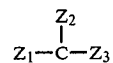

and salts thereof
wherein $Z_1$, $Z_2$ and $Z_3$ are benzyl groups substituted in one or more positions with hydrogen groups, carboxyl groups or hydroxyl groups.

* * * * *